(12) United States Patent
Silver

(10) Patent No.: US 10,034,813 B1
(45) Date of Patent: Jul. 31, 2018

(54) SYSTEM AND METHOD FOR A DEEP TISSUE MASSAGER

(71) Applicant: Alan H. Silver, Coral Springs, FL (US)

(72) Inventor: Alan H. Silver, Coral Springs, FL (US)

( * ) Notice: Subject to any disclaimer, the term of this patent is extended or adjusted under 35 U.S.C. 154(b) by 527 days.

(21) Appl. No.: 14/215,377

(22) Filed: Mar. 17, 2014

Related U.S. Application Data

(60) Provisional application No. 61/801,133, filed on Mar. 15, 2013.

(51) Int. Cl.
*A61H 7/00* (2006.01)
*A61B 19/00* (2006.01)

(52) U.S. Cl.
CPC ......... *A61H 7/004* (2013.01); *A61B 19/2203* (2013.01)

(58) Field of Classification Search
CPC .......... A61H 7/00–7/002; A61H 7/004–7/005; A61H 23/00–23/02; A61H 23/0254–23/0263; A61H 2023/0281; A61H 39/007; A61H 2201/12–2201/1223; A61H 2201/1671
See application file for complete search history.

(56) References Cited

U.S. PATENT DOCUMENTS

| | | | |
|---|---|---|---|
| 3,252,775 A * | 5/1966 | Tocci-Guilbert ....... | B24D 13/02 264/54 |
| 4,102,334 A | 7/1978 | Muchisky | |
| 4,175,548 A * | 11/1979 | Henry ................. | A61H 7/001 601/1 |
| 4,495,940 A | 7/1985 | Takaishi | |
| 5,083,552 A | 1/1992 | Lipowitz | |
| 5,437,607 A * | 8/1995 | Taylor ................. | A61H 1/00 5/915 |
| 5,940,888 A * | 8/1999 | Sher ................... | A61H 7/001 2/109 |
| 6,648,904 B2 * | 11/2003 | Altshuler ............. | A61F 7/02 492/46 |
| 6,758,826 B2 | 7/2004 | Luettgen | |
| 9,446,260 B2 * | 9/2016 | Jagger ................ | A61N 5/0613 |
| 2004/0077978 A1 * | 4/2004 | Nelson ............... | A61H 23/0263 601/70 |
| 2005/0148910 A1 | 7/2005 | Skover | |
| 2007/0123808 A1 * | 5/2007 | Rhoades ............. | A45D 24/007 601/73 |
| 2007/0219474 A1 * | 9/2007 | Wen .................. | A61H 1/005 601/49 |
| 2007/0282228 A1 * | 12/2007 | Einav ................ | A61B 5/7475 601/33 |
| 2008/0267447 A1 * | 10/2008 | Kelusky ............. | G06F 19/3481 382/100 |
| 2009/0204061 A1 | 2/2009 | Pomposelli et al. | |
| 2009/0222024 A1 * | 9/2009 | Naldoni ............. | A61B 17/54 606/131 |

(Continued)

FOREIGN PATENT DOCUMENTS

WO        82/01923  A1    6/1982

*Primary Examiner* — Rachel T Sippel
(74) *Attorney, Agent, or Firm* — Fleit Gibbons Gutman Bongini Bianco PL; Jose Gutman

(57) ABSTRACT

A system, device, and method for therapeutic deep tissue massage is disclosed. The therapeutic deep tissue massage device includes an apparatus for use in therapeutic massage applications in which forces are provided to an outer surface of the human body and subcutaneously within human tissues.

21 Claims, 5 Drawing Sheets

(56) References Cited

U.S. PATENT DOCUMENTS

| | | | |
|---|---|---|---|
| 2011/0118641 A1* | 5/2011 | Gomez, Jr. | A61H 1/0292 602/32 |
| 2012/0071794 A1* | 3/2012 | Karni | A61B 34/30 601/2 |
| 2013/0131562 A1* | 5/2013 | Wu | A61H 7/007 601/112 |

* cited by examiner

SYSTEM AND METHOD FOR A DEEP TISSUE MASSAGER

CROSS-REFERENCE TO RELATED APPLICATIONS

This application is based upon and claims priority to U.S. Provisional Patent Application Ser. No. 61/801,133, filed on Mar. 15, 2013, the disclosure of which is hereby incorporated by reference in its entirety.

BACKGROUND

The present disclosure generally relates to deep tissue massagers, and more particularly relates to an apparatus for use in therapeutic massage applications in which forces are provided to an outer surface of the human body and subcutaneously within human tissues.

Traditional massage therapy has not changed significantly since its inception in 2330 BC. Frequently the daily demands placed on many humans today produces pain in the neck, shoulders, lower backs, legs and more. These pains are a result of overworked muscles that never fully return to a relaxed state, but instead are overworked repeatedly until they are contracted so as to better protect the muscle tissues to from being strained or torn. These repeated patterns of overuse frequently lead to a constant state of contraction or chronic muscle spasm.

Traditional massage therapy only relieves these problems for short periods of time, and is ineffective on deep muscle spasms unless numerous massages are scheduled over a period of days, weeks or months. Human Skin is comprised of a.) the epidermis, b.) the dermis, and c.) the hypodermis. More recent massage techniques employ the means to promote circulation within the blood and lymphatic vessels present in the skin, but are largely ineffective in doing so.

In order for professional massage, sports or physical therapists to be most effective, they must be very physically fit, as to provide an effective deep tissue massage requires exerting great forces for long periods of time. Additionally, professionals must provide a series of deep tissue massages in succession, which requires even greater physical stamina, that frequently result in repetitive stress or other injuries to the professional.

In using conventional devices and methods for deep tissue massage, it has been found inconvenient, for example, that in an effort to penetrate severe muscle spasms, even professional therapists can inflict pain, or cause bruising to the skin in an effort to penetrate a severe or deep muscle spasm. Motorized massage devices typically have had a contact surface arrangement including a composition of rigid plastic or terry cloth in direct contact with a patient's skin which during operation of the device can result in chafing, abrasion, or bruising of the massaged skin or tissue. Additionally, the terry cloth or a similar pad cover can be prone to disintegrate into airborne particles, which when breathed in, causes respiratory complications to the sinuses, throats and lungs in both the therapist and the patient.

BRIEF SUMMARY

According to an embodiment of the present disclosure, a motorized therapeutic massage device is disclosed. The device includes an electrical motor having a motor drive shaft, disposed within an enclosure; and a contact surface arrangement coupled to said motor drive shaft, by means of a transfer member disposed within an enclosure, that is offset from the center axis of the motor drive shaft and a center axis of the contact surface arrangement; and wherein the motor and driveshaft are coupled to drive the contact surface arrangement to impart both random orbital oscillating motion and percussive motion to the contact surface arrangement; and further wherein the contact surface arrangement creates a penetrating shockwave subcutaneously through human or animal muscle tissue, and minimizes the frictional engagement of skin or garments covering the skin, and minimizes temperature increase of the contact surface arrangement and the skin resulting from the frictional engagement.

In an embodiment of the present disclosure, a method of applying mechanical oscillating energy through human or animal muscle tissue comprises: contacting an area of skin covering human or animal muscle tissue, with a contact surface arrangement of a mechanical oscillation treatment device and applying power to a motor of said device while said contact surface arrangement is in contact with the area of human or animal tissue to apply random orbital oscillating energy to the tissue by oscillating the contact surface arrangement in a direction approximately parallel to a surface of the tissue in a random orbital motion having a variable orbit diameter to induce shearing and stretching forces in the tissue.

In an embodiment of the present disclosure, a method of applying mechanical oscillating energy through human or animal muscle tissue comprises: contacting an area of skin covered human or animal muscle tissue, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction approximately perpendicular to a surface of the tissue in a random orbital motion having a variable orbit diameter to induce shearing and stretching forces in the tissue.

In an embodiment of the present disclosure, a method of applying mechanical oscillating energy through human or animal muscle tissue comprises: contacting an area of skin covered human or animal muscle tissue having muscle tension or soreness, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction having both parallel and perpendicular components to a surface of the tissue in a random orbital motion to induce shearing and stretching forces in the tissue.

BRIEF DESCRIPTION OF THE DRAWINGS

The accompanying figures, in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

Introduction

Figure 1:
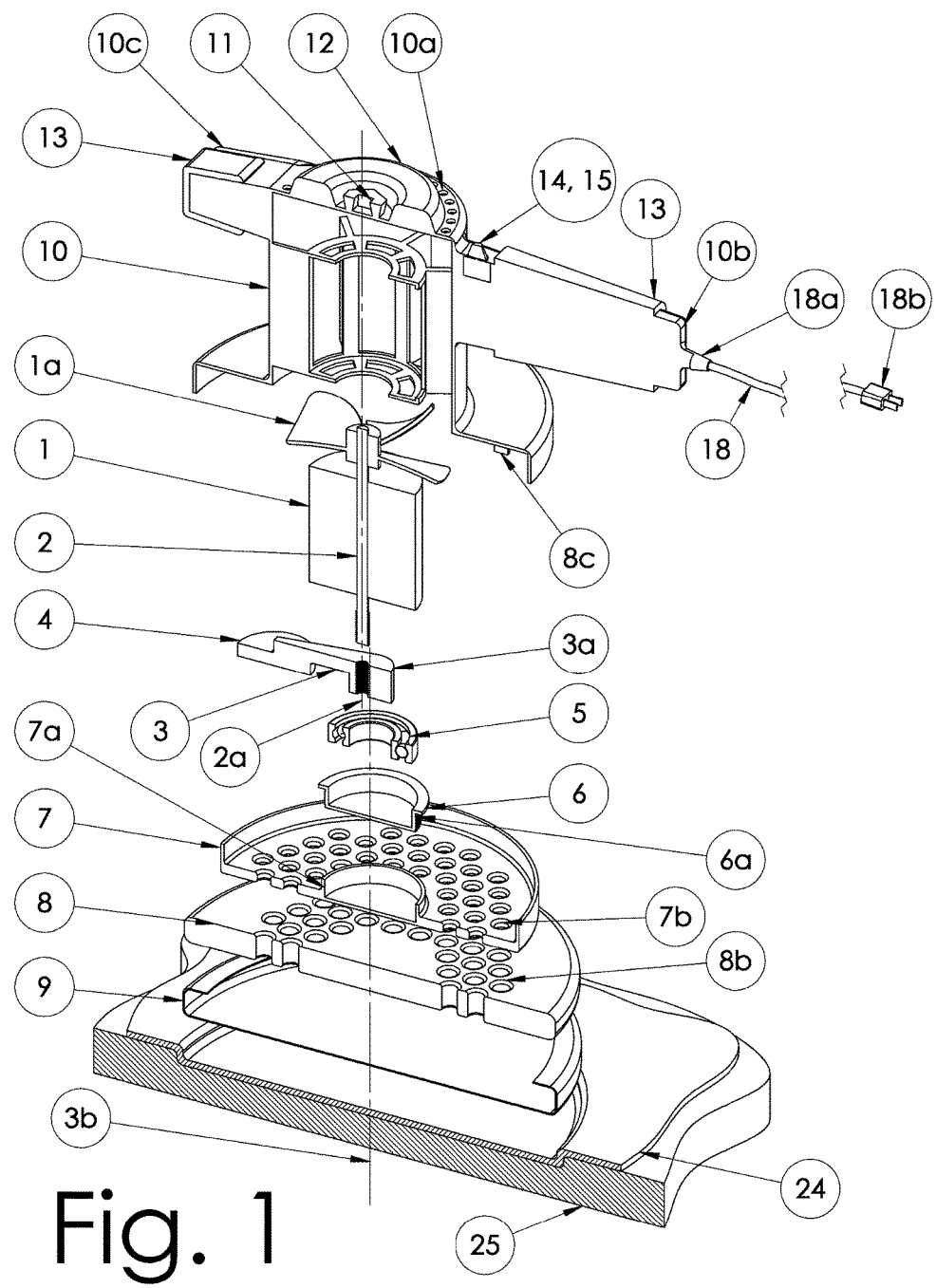
FIG. 1 is an exploded view of a motorized therapeutic massage device, according to one embodiment of the present disclosure.

Before explaining the disclosed embodiments of the present invention in detail it is to be understood that the invention is not limited in its application to the details of the particular arrangement shown since the invention is capable of other embodiments. Also, the terminology used herein is for the purpose of illustration and description and not of limitation.

An embodiment of the invention will reduce massage therapy treatment to a small number of sessions, possibly of less than a single hour each, providing a very recuperative and effective deep tissue massage to a patient.

According to an embodiment, a motorized massage device is provided with a contact surface arrangement having a low coefficient of friction. Previous motorized massage devices typically had an oscillating contact surface directly contacting a patient's skin where the contact surface included a composition of rigid plastic or terry cloth that can result in chafing, abrasion, or bruising of the massaged skin or tissue. Additionally, terry cloth or a similar pad cover is prone to disintegrate into airborne particles, which when breathed in, causes respiratory complications to the sinuses, throats and lungs in both the therapist and the patient.

According to an embodiment, a small, portable solution is provided as an alternative to using equipment that is difficult, if not impossible to transport to the user, or which may require the user to travel to the equipment. It is much more practical to employ the use of a small, portable solution in a users home, for example, than having the user travel to the massage therapy equipment to undertake numerous, less effective treatments.

One or more embodiments of the present invention provide an apparatus that improves over the prior art by:

providing a portable massage device that allows a user or a professional to treat himself or a patient in an office or at home;

providing a means for chiropractic physicians to relax his or her patients prior to providing adjustment(s);

providing a quickly detachable massage pad with a substantially smooth surface that minimizes the frictional engagement of the patients skin, and may be used thru a garment the patient is wearing over his skin, or upon bare skin;

providing a massage pad cover that when in use provides a further cooling effect to a contact surface arrangement of the massage device by drawing in cooling ambient air between the contact surface arrangement and the user's skin;

focusing on risks associated with chafing and burning of the skin, and with hair entanglement;

provide for a means to detect the pressure and temperature of the contact surface and display over limit pressure and temperature conditions;

providing a means to prevent objects such as hair and clothing from becoming entangled within the unit;

providing a means to bear down on a pressure pad disposed on the enclosure to achieve an even greater depth of massage, without causing pain or injury to the user or massage therapist;

providing a fan within the unit to cool the device and provide for a smaller, lighter, safer, more maneuverable and longer lasting product;

providing a means to attach accessories to the massage device to allow additional features and accessories to be used with the device; and providing additional safety features that are not found on existing products, so as to that prevent injury to the users and damage to the apparatus. (hair and clothes entanglement, temp protection, rev limiter, pressure pad, grip pads, longer power cord, communication system).

Various embodiments of the present system improve over the prior art by:

providing a means to mount the device to and communicate with a computer controlled, 5 axis CNC (computer numerically controlled) motorized machine;

providing a means to input relative coordinate data from, and to capture topographical data of the individual being treated and communicate it to the CNC motorized machine;

providing a means for patient and therapist to verbally communicate in a high noise environment when a patient is receiving treatment; and providing a means to store and communicate data including, but not limited to position, pad pressure, temperature, rate of rotation, rate of travel, run time etc.

Definitions

The following terms, when used herein and capitalized or otherwise, are defined as follows:

"Contact Surface": See "Massage Pad":

"Massage Pad": Portion of the Device that couples the "Random orbital oscillating" motion, and the "Percussive" motion produced by the motor of the device, and their respective "Random orbital oscillating" and "Percussive" forces to human and animal skin and tissue. Even though it is understood that the "Massage Pad" does not physically contact either Skin or Tissue, as defined below, it is understood that the "Massage Pad Cover" does not inhibit any motion or forces, but acts to minimize the frictional engagement of the "Massage Pad" against the human or animal skin. As such, the "Massage Pad" and the "Massage Pad Cover" may be individually or collectively used interchangeably, or also be referred to as being part of the "Contact Element" or "Contact Surface Arrangement".

"Skin": Generally used to describe naked human skin. Also may include, but not be limited to the expanse of human skin, and the underlying "Tissue" disposed in proximity of the general area. Also may include the skin of animals, including but not limited to horses.

"Tissue": Generally used to describe human muscle tissue. Also may include, but not be limited to the skin, muscle fascia, tendons, cartilage, fat, blood vessels, lymphatic vessels, lymph nodes, internal organs, and animals.

"User": Generally used to describe a person operating the device. Also may include, but not be limited to a person using the machine on him or herself, or on another individual or an animal. Also may include, but not be limited to chiropractic physicians or massage, sports, or physical therapists, and a group or multiple groups of people. Also may include, but not be limited to one user receiving treatment from another individual, therapist, trainer, rehabilitation tech, or physician, where that user may be referred to as a "Patient".

"Muscle Spasm": Generally used to describe a sudden, involuntary contraction of a muscle, a group of muscles, or a similarly sudden contraction of an orifice. Also may include, but not be limited to a muscle cramp which is often accompanied by a sudden burst of pain, or involuntary muscle contractions, which may be more serious, depending on the cause. Also may include, but not be limited to insufficient hydration, muscle overload, and absence of electrolytes. Spasmodic muscle contraction may be due to a large number of medical conditions, including, but not limited to dystonias, or Hypertonic muscle spasms—a state of chronic, excessive tension in a resting muscle.

"Motor": Generally used to describe a motor powered by A/C, but may include, but not be limited to a DC motor, a reversible A/C or DC motor, a stepper motor, or any motor that is well understood by those of ordinary skill.

Description of Examples

Various embodiments of the present disclosure relate to an apparatus for use in therapeutic massage applications in which forces are provided to an outer surface of the human body and subcutaneously within human tissues. The apparatus, according to one example, includes a covered, motor driven pad that imparts both random orbital and percussive forces to the skin and tissue of a human body in various contact arrangements between a massage pad and the skin and its underlying tissue.

Figure 2:
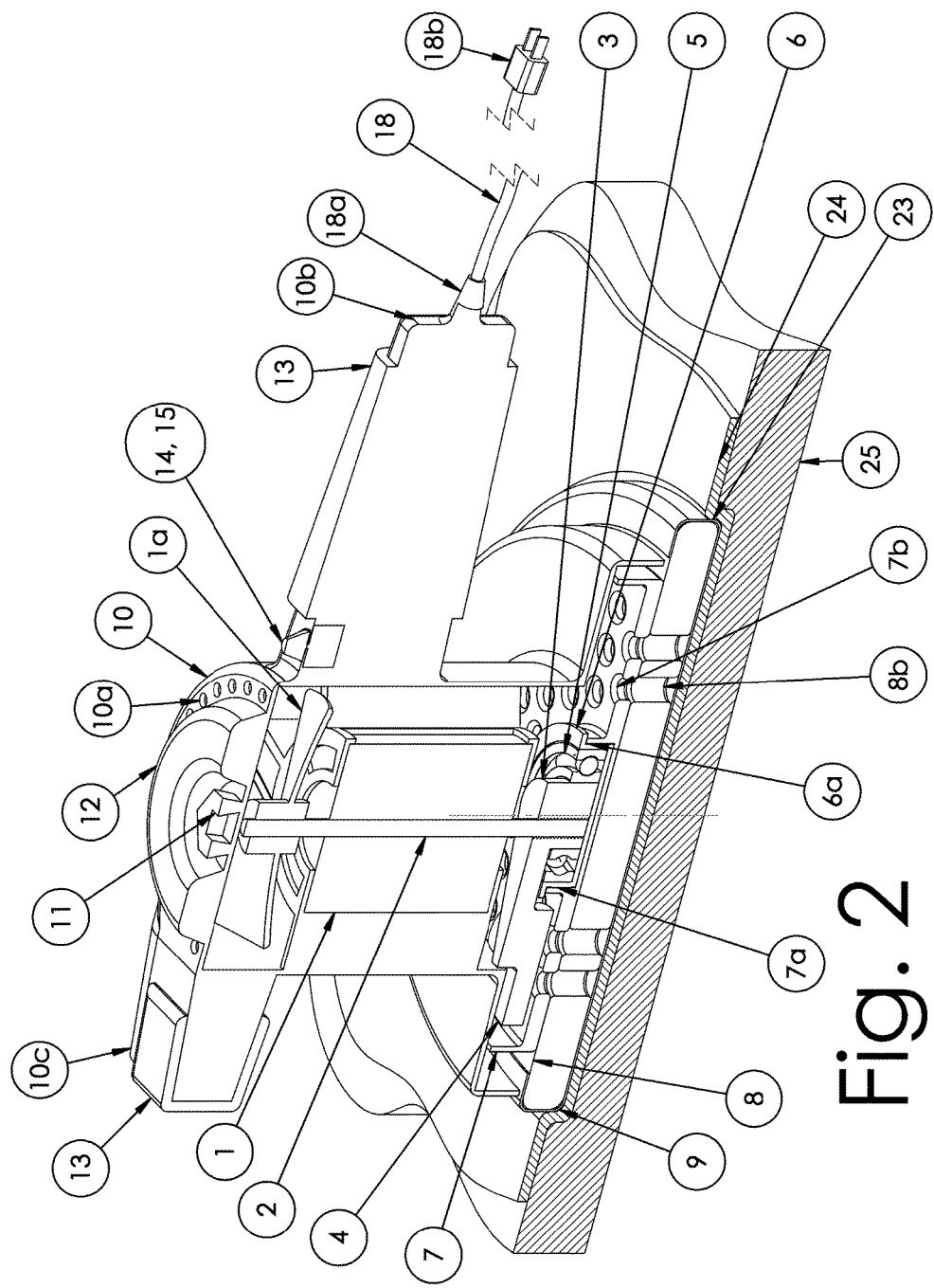
FIG. 2 is a cross sectional view of the motorized therapeutic massage device of FIG. 1.

Refer now to FIGS. 1 and 2, in which FIG. 1 shows an exploded view of one example embodiment of a portable, hand held, motorized therapeutic massage device and FIG. 2 shows a cross-section thereof. A motor 1 has a cooling fan 1a and a motor drive shaft 2 that delivers mechanical energy to a transfer member 3 having an offset hub 3a with center axis 3b. The transfer member 3 has a counter weight 4 and the offset hub 3a within an inner bearing race of a ball bearing assembly 5, also consisting of ball bearings and an outer bearing race which couple to quick disconnect mounting plate 6. A contact surface 8, 9, according to the present example, is coupled to the transfer member 3 by the offset hub 3a and has a center axis coincident with the center axis 3b of the offset hub 3a. The contact surface 8, 9, is coupled to the motor drive shaft 2 by means of the transfer member 3. The center axis 3b of the offset hub 3a and the center axis of the contact surface 8, 9 are offset from the center axis 2a of the motor drive shaft 2. The contact surface 8, 9, in the example, comprises a multilayered component including, but not limited to a layer of cellular foam or rubber, and a covering substantially including, but not limited to leather or woven cloth and vinyl. The quick disconnect mounting plate 6 has a quick disconnect part A 6a, that mates with quick disconnect part B 7a, disposed on a massage pad mounting plate (or rigid disk) 7. A plurality of sensors in the motorized therapeutic massage device can measure at least one state of properties associated with the contact surface 8, 9, including, but not limited to temperature (see, for example, temperature sensor 8c in FIG. 1) or pressure (sensor not shown). According to certain embodiments, the plurality of sensors is coupled to an indicator or indicators in the motorized therapeutic massage device. A shutoff is configured to be activated when one or more of the plurality of sensors exceeds a pre-set value.

According to this embodiment, the quick disconnect is shown as one example, and is not intended to limit other possible configurations, including, but not limited to reversing the motor 1, or having a lock, a detent, a turret or other style of chuck. A massage pad 8 is disposed adjacent to the massage pad mounting plate (or rigid disk) 7. The massage pad 8 may be composed of one or more materials, including but not limited to, cellular foam or rubber, expanded polyurethane, cellular rubber or a semi-rigid foam. Vent holes 7b and 8b provided in the massage pad mounting plate 7 and the massage pad 8 respectively, allow cool air to be pulled from the top of the unit through the enclosure air vents 10a by the cooling fan 1a to cool the motor 1, the massage pad 8 and the massage pad cover 9. Gripping the primary handle 10b and the secondary handle 10c, where in this example the secondary handle 10c has safety grip pads 13, the user can direct position the enclosure 10, so as to couple the force from the massage pad 8 thru the massage pad cover 9, the patients' garments (not shown), the patient's skin 24, and into the patient's muscle tissue 25. A pressure pad 12 disposed on the enclosure provides a means to bear down on to achieve an even greater depth of massage, without causing pain or injury to the user or massage therapist.

In a first arrangement, referring to FIGS. 1 and 2, for example, and not for limitation, the large surface area of the pad 8 parallel to the body of the patient is shown contacting the skin surface of the patient and providing shearing and stretching random orbital motion across the skin, while pressed into the patient's tissue with the large flat portion of the massage pad 8 and the massage pad cover 9 pressed into the muscle tissue 25. In this position, the flat portion of the massage pad 8 will impart a random orbital oscillating motion (i.e., the random orbital oscillating motion having a variable orbit diameter) to the skin 24 that it is in contact with, and the muscle tissue 25 that it is pressed into. Mainly friction force between the lateral pad surface and the skin surface at the contact area transfers lateral vibratory vibration from the pad 8 to the skin of the patient. With every rotation of the massage pad 8, shearing and stretching forces are coupled into the muscle tissue 25. In one example embodiment, the massage pad cover 9 is constructed of a flexible covering of one or more layers, and includes but is not limited to one or more materials such as leather, Teflon, woven cloth, or vinyl.

Continuing with the example, in a second arrangement, an edge surface (i.e., other than the large flat portion) of the pad 8 contacting the skin 24 provides deep pulsating vibrations into the skin surface typically at a normal or near normal axis with the skin surface.

Figure 3:
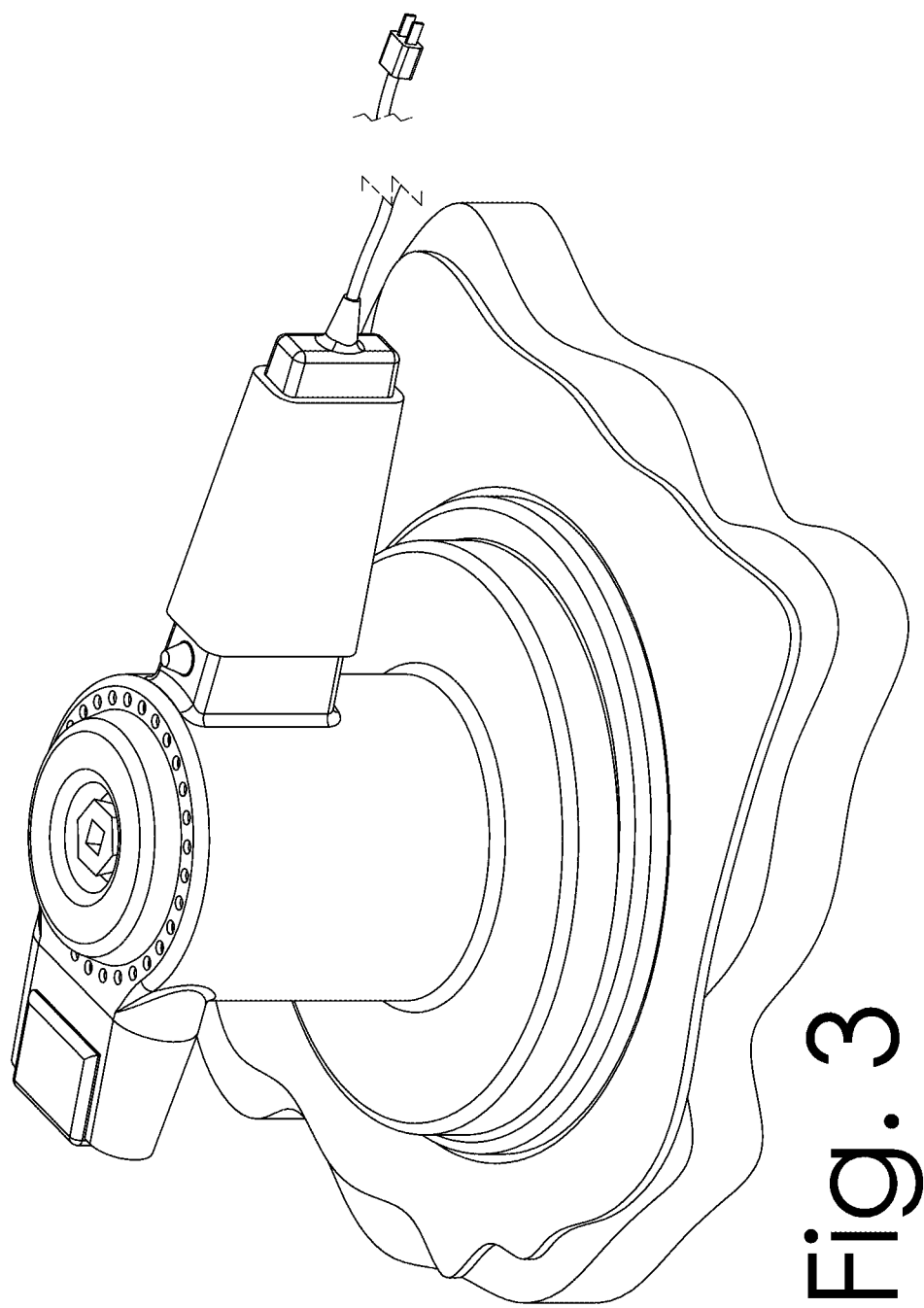
FIG. 3 is a perspective view of the motorized therapeutic massage device of FIG. 1.

With reference to FIGS. 1, 2, and 3, an exploded view, a cross-sectional view, and a perspective view, of an example embodiment of a motorized therapeutic massage device are shown, for example, and not for limitation, illustrating the mechanically engaged human skin and it's associated human tissue, created by the massage pad's cover when pressed into an expanse of the human skin and tissue.

Analysis using a stroboscopic light source has shown that this force propagates approximately 6 inches through the muscle tissue, and is visible as ripples in a wave. Because the human body is composed mostly of water, this should not be a surprise.

In physics, the phenomenon of resonant frequency will show that based on the density of the muscle tissue 25, there will be a preferred oscillating motion revolutions per minute (RPM) that will propagate a wave further than all other RPM's.

As an example, if a professional football player were suffering from a pulled thigh muscle, any exertion on the muscle would cause the muscle to contract into a muscle spasm. This is the body's self defense method, in which the thigh muscle is being contracted to prevent a more serious injury such as a muscle tear. The football player could loosen up the thigh muscle using a consumer version at his home, several times a day, largely by using the device in a random orbital oscillating force. The force on the muscle would cause delivery of compounds including but not limited to oxygen, blood and lymphatic fluids through the vessels and tissues, healing the injury and reducing swelling, and flushing toxins including but not limited to lactic acid out of the muscle tissue. This increased blood flow would further warm the area, causing vessels to stay dilated longer, thus helping the football player's body, in this example, to continue healing itself. As the muscle spasm eases, the player would be able to better tolerate a more aggressive percussive force, able to penetrate deeper into the tender muscle, and continued therapy thru a sports rehab trainer, to enable the player to play for a game that would otherwise not be able to play.

By promoting the circulation of substances in the body, many medical conditions can be improved. Patients having heart disease, diabetes, phlebitis, for example, and other illnesses resulting in compromised circulation of fluids including but not limited to blood and lymphatic fluid, and congestion within lungs and tissues would be benefited by the use of such therapy. The improvement of circulation would cause congested blood vessels and tissues to be flooded with oxygen, and waste products or toxins including but not limited to lactic acid to be flushed from the tissues and lymphatic vessels. An example of this would be forcing the blood from one's calves upwards towards the heart to prevent edema in the legs. The resulting reduction in swelling in the calves would allow increased flow of blood to continue to flush the calve muscles with blood, thereby opening up a pathway for the body to allow the circulation of blood and lymphatic fluids to continue to nourish and flush tissues that would otherwise fail to be nourished and flushed as effectively.

An embodiment of the disclosure is further related to massage devices used to reduce muscle spasms, by both warming up muscle tissues both prior to physical activity, and relaxing muscle tissues after physical activity. Muscle spasms that are so deep within large muscle tissues may be impossible to be treated using conventional massage therapy. The prior art discloses numerous massage devices and methods that have been used to treat muscles, muscle spasms, improve circulation, promote the flushing of waste products from tissues, and break up bronchial secretions, using massaging circular oscillations across the skin and tissue and alternatively percussive types of force directed generally normal to and into the skin and tissue.

Many prior art vibrators and massage devices require massage directly to the skin, and as such, are and are not effective for prolonged use, as chafing or burning of the skin can result. Many of these devices and treatments pose the risk of hair or clothes entanglement, and therefore require the patient not be clothed. Additionally, prior art devices are prone to overheating, forcing the user to wait between uses, to allow the device to cool down, or otherwise risk burning out the device, thereby requiring the device to be repaired or replaced. Frequently the prior art devices are mounted to a wall or disposed within a cart, making it difficult, if not impossible to transport the device. For at least these reasons, many prior art devices require the patient to travel and come to be treated at a location where the treatment equipment is located.

Figure 4:
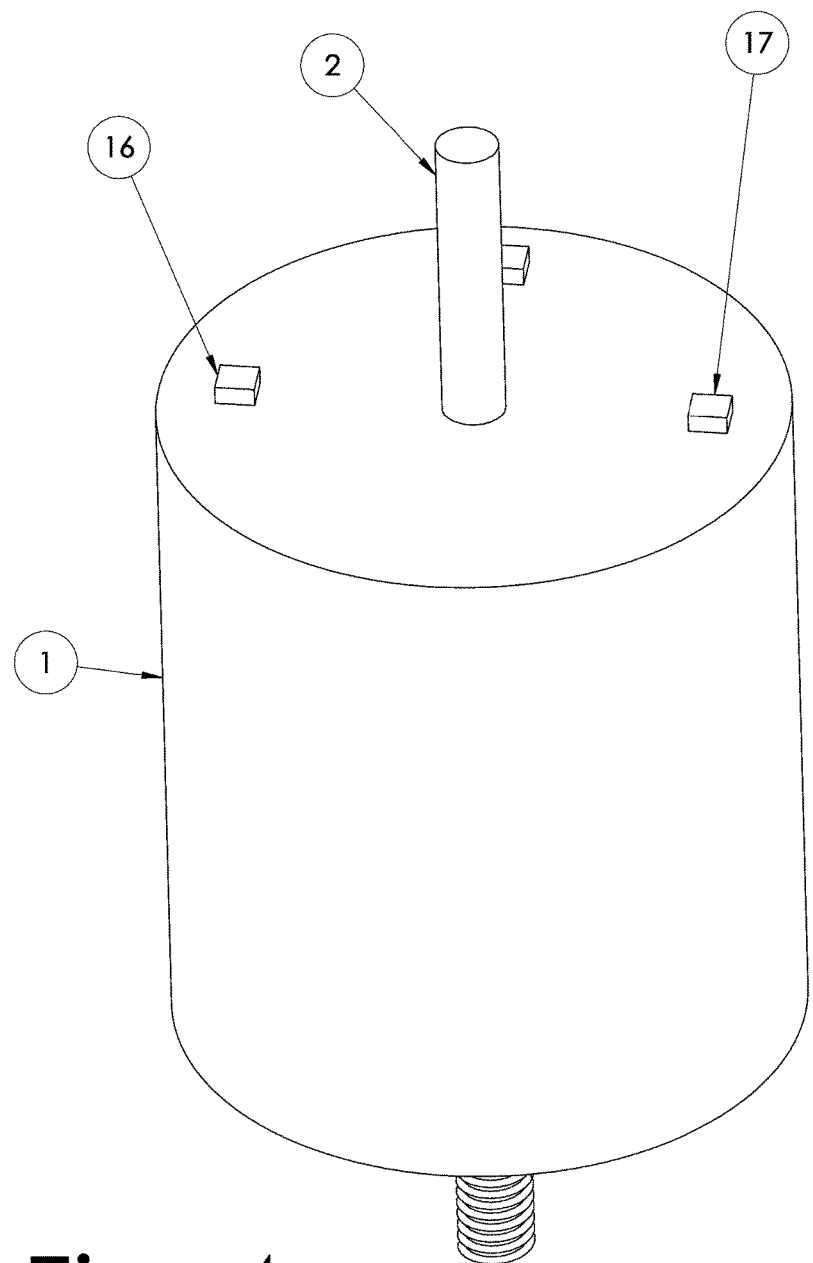
FIG. 4 is a perspective view of a motor in the motorized therapeutic massage device of FIG. 1.
Figure 5:
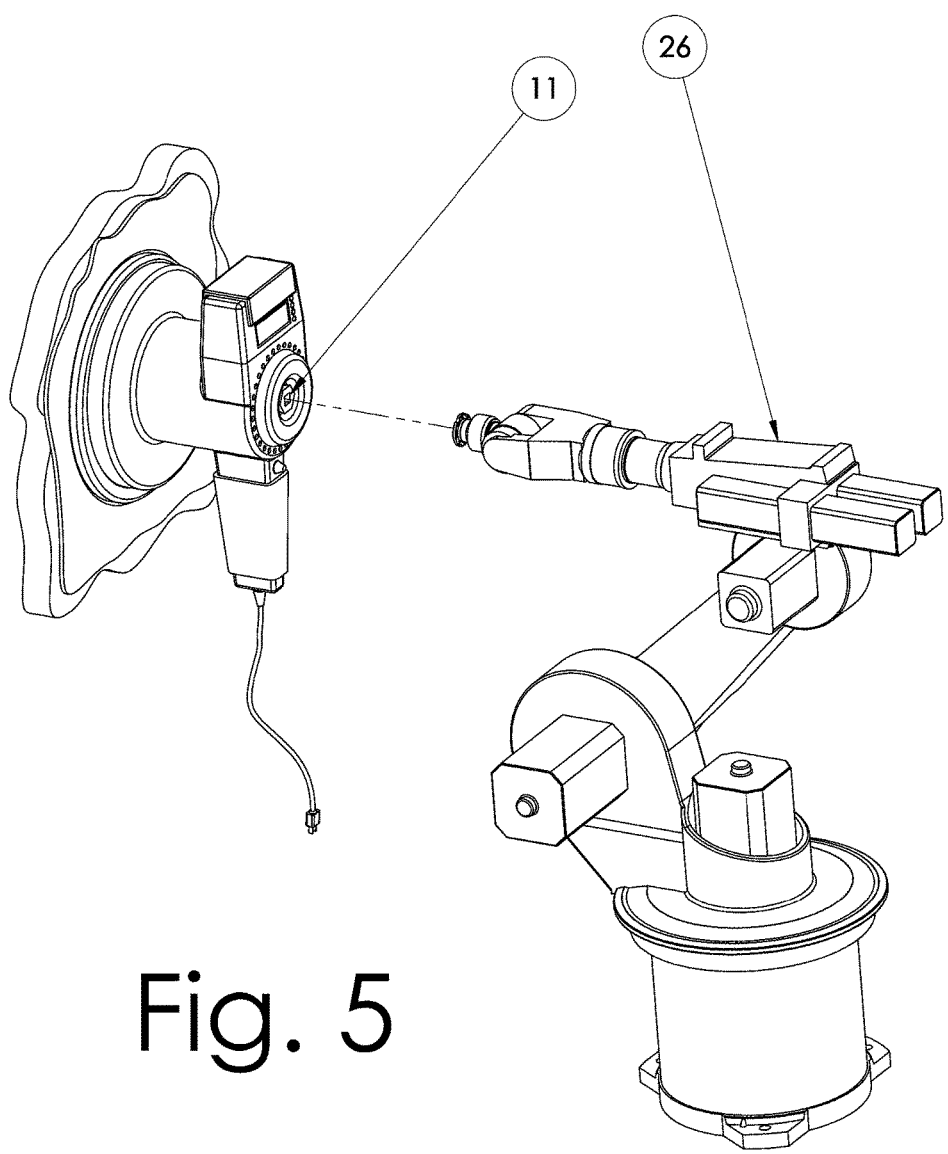
FIG. 5 is a perspective view of an accessory mount of the motorized therapeutic massage device of FIG. 1.

Referring again especially to FIG. 1, in the present example, AC power is provided to the motor 1 by a power cord 18, having both a plug 18b and a strain relief 18a. The AC power is switched by power switch 14 and the motor 1 is allowed to run at variable speeds by means of variable speed control 15, which in this embodiment, by example is incorporated into power switch 14, and includes, but is not limited to, a rheostat, a solid state controller, or a multi-position switch. Additionally, as shown in FIG. 4, other aspects may include but not be limited to high temperature protection 17 shutting off the motor 1 when monitored temperature indicates the motor 1 is overheating, or rev limiter 16, preventing excessive RPM of the massage pad 8, should the operator lift the contact surface away from a patient's body part being treated. An embodiment of the device can provide a means to cool the massage pad 8 by any one or more, but not limited to, the vent holes 7b and 8b and arrangement that has already been discussed above, a Peltier solid state cooling chip, or a secondary Fan, or the like.

FIGS. 1, 2, 3, and 5 show accessory mount 11, which allows accessories to be attached to the unit for other purposes, or the unit to be attached for other purposes, including, but not limited to mounting to a massage chair, a wall mount, or on a robotically controlled system 26.

Another embodiment includes a mobile service including but not limited to a massage therapist coming on site to provide massage services at various venues, including workplaces or conventions, performing massage services on attendees positioned on both massage chairs and massage tables.

Other embodiments include attachment of the device to a 5-axis robotically controlled system 26, having an emergency stop switch (not shown), which is well known in the manufacturing industry, and is routinely used for computer numerically controlled (CNC) milling processes, using 3-dimensional space, as defined by the Cartesian coordinate system. This aspect includes, but is not limited to a computer controlled robotic arm, a combination of gantry arms, or the like, attached to the massage device discussed above. An example embodiment of such a system stores patient profiles that for each patient can include, but is not limited to, account information, medical records, body topography, preferences for programmed default and personalized massage paths, RPM speeds, rate of travel (feeds), contact surface pressure, angles of tilt and rotation, and exclusion areas.

Such an embodiment may include either manually mapping the topography of the patient, using methods including but not be limited to capturing spatial data points moving the massage pad over the body, by means of a joystick controller to mapping the topography of the patient using a laser scanner. Additionally, audio and video data can be captured when a patient is receiving treatment. Another aspect may include, but not be limited to, a plurality of massage centers located in airports or other locations connected via a computer network that could provide the patient at any of the locations with individualized massage therapy program. This would allow weary travelers to receive their desperately needed massage just the way they like it, no matter where in the world they are.

Like the mobile service described above, one or more robotically controlled systems 26 could be disposed within a mobile vehicle, including but not limited to a van, a mobile home, a recreational vehicle, or travel trailer. One such embodiment includes, but is not limited to: sporting events, concerts, special events, and corporate events. Patient profiles would be accessed via wireless cellular networks.

One embodiment of such a system can include, but is not limited to, a web based scheduling system that allows the user to find locations, schedule appointments for both manual and robotic massage sessions, and pay via the user's smart phone.

One should note that the above described various example embodiments of the invention, are for illustration purposes only, and are not for the purpose of limiting its scope. The various examples teach various changes in form, details, improvements and other embodiments that may be equally effective. Such improvements are intended to be part of this disclosure without departing from the scope of the invention as defined by the appended claims.

Non-Limiting Examples

Flowchart and block diagrams that may be shown in the Figures and/or described herein illustrate the architecture, functionality, and operation of possible implementations of systems, devices, and methods, according to various embodiments of the present invention. In this regard, each block in a flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present specification may describe components and functions implemented in the embodiments with reference to particular standards and protocols, the disclosure is not limited to such standards and protocols. Each of the standards represent examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. A motorized therapeutic massage device comprising:
an electrical motor having a motor drive shaft, disposed within an enclosure,
a contact surface arrangement having an outer surface and an inner surface that faces inside the enclosure and forms one side of the enclosure, the contact surface arrangement being coupled to said motor drive shaft by means of a rigid transfer member having an offset hub coupled to the motor drive shaft, the offset hub being directly coupled and rotationally coupled to a bearing assembly and thereby rotationally coupled to the contact surface arrangement, a center axis of the motor drive shaft being offset from a center axis of the offset hub which is coincident to a center axis of the contact surface arrangement, and wherein the inner surface of the contact surface arrangement, the motor drive shaft, the transfer member, the offset hub, and the bearing assembly, being disposed within the enclosure, and wherein the motor and driveshaft are coupled to the contact surface arrangement to rotationally drive the contact surface arrangement to impart rotational motion including both random orbital oscillating motion and percussive motion to an outer surface of the contact surface arrangement, and wherein the outer surface of the contact surface arrangement comprises material with a low coefficient of friction to reduce frictional engagement, and reduce temperature increase resulting from the frictional engagement, of the outer surface of the contact surface arrangement and a surface of skin of a human or animal while the outer surface of the contact surface arrangement is moving laterally relative to the surface of the skin, and wherein the contact surface arrangement is adapted to, in response to the motor and driveshaft rotational drive force rotationally driving the contact surface arrangement, and while the rotationally moving outer surface of the contact surface arrangement is contacting with, while moving laterally relative to, a surface of a skin of a human or animal and being pressed into the skin and subcutaneous human or animal muscle tissue underlying the skin, imparting to the skin and subcutaneous muscle tissue mechanical oscillating percussive shockwaves for penetrating the skin and subcutaneous muscle tissue to induce shearing and stretching forces in the muscle tissue, while reducing lateral frictional engagement of the laterally moving outer surface of the contact surface arrangement contacting the surface of the skin or garments covering the skin; and wherein a first set of vent holes in at least one wall of the enclosure is arranged on one side of a cooling fan located within the enclosure and the inner surface of the contact surface arrangement is arranged on an opposite side of the cooling fan to move and direct air through the enclosure and thereby to and/or from the contact surface arrangement to cool the contact surface arrangement at its outer surface which is adapted to contact the surface of the skin.

2. The motorized therapeutic massage device of claim 1, wherein the contact surface arrangement is coupled to said motor drive shaft, and offset from the center axis of the motor drive shaft, by means of the transfer member which includes a counterweight disposed to impart random orbital oscillating motion and/or percussive motion to the contact surface arrangement.

3. The motorized therapeutic massage device of claim 1, wherein said random orbital oscillating motion has a variable orbit diameter.

4. The motorized therapeutic massage device of claim 1, further comprising at least one sensor to measure at least one state of properties associated with the contact surface arrangement, comprising temperature.

5. The motorized therapeutic massage device of claim 1, wherein at least one sensor in the device for measuring at least one state of properties associated with the contact surface arrangement, the at least one sensor is coupled to an indicator or indicators in the device.

6. The motorized therapeutic massage device of claim 1, further comprising a shutoff configured to be activated when one or more sensors exceed a pre-set value.

7. The motorized therapeutic massage device of claim 1, wherein the contact surface arrangement comprises a multilayered component arrangement comprising at least one of a layer of cellular foam, cellular rubber, expanded polyurethane, semi-rigid foam, and a covering comprising at least one of leather, Teflon (also known as polytetrafluoroethylene), woven cloth, and vinyl.

8. The motorized therapeutic massage device of claim 1 wherein the contact surface arrangement comprises a massage pad that can be quickly disconnected from the device by a quick disconnect mounting arrangement.

9. The motorized therapeutic massage device of claim 1, further comprising:

a second set of vent holes provided in the contact surface arrangement which, while the contact surface arrangement is rotationally moving, operate to have air pulled through the second set of vent holes to cool the contact surface arrangement at its outer surface which is adapted to contact the surface of the skin.

10. The device of claim 1, the therapeutic massage device being communicatively coupled to and disposed upon a robotically controlled system to provide a full body massage to a patient by the robotically controlled system moving and controlling the motorized therapeutic massage device on the patient's body and having the ability by such movement and control to tilt, rotate, and move the therapeutic massage device thru space in three spatial dimensions.

11. The device of claim 10, wherein the robotically controlled system, responsive to executing computer instructions, performs operations comprising one or more of the following:

contacting an area of skin covering human or animal muscle tissue, with a contact surface arrangement of a mechanical oscillation treatment device and applying power to a motor of said device while said contact surface arrangement is in contact with the area of human or animal tissue to apply random orbital oscillating energy to the tissue by oscillating the contact surface arrangement in a direction approximately parallel to a surface of the tissue in a random orbital motion having a variable orbit diameter to induce shearing and stretching forces in the tissue;

contacting an area of skin covered human or animal muscle tissue, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction approximately perpendicular to a surface of the tissue in a random orbital motion having a variable orbit diameter to induce shearing and stretching forces in the tissue; and contacting an area of skin covered human or animal muscle tissue having muscle tension or soreness, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction having both parallel and perpendicular components to a surface of the tissue in a random orbital motion to induce shearing and stretching forces in the tissue.

12. The device of claim 11, wherein the robotically controlled system, responsive to executing computer instructions, performs operations comprising:
capturing audio and video data of the treatment when a patient is receiving mechanical oscillation treatment.

13. The device of claim 11, wherein the robotically controlled system, responsive to executing computer instructions, performs operations comprising:
communicating via a computer network with other robotically controlled systems remotely located at other massage treatment centers, the other robotically controlled systems being coupled to other therapeutic massage devices, and the robotically controlled systems at the different locations sharing patient profiles to provide a patient at any of the locations with one or more individualized massage therapy programs.

14. The device of claim 13, wherein each of the robotically controlled systems coupled to a motorized therapeutic massage device being disposed within respective mobile operations vehicles located at the different locations and communicating via the computer network with each other.

15. The device of claim 11, wherein the robotically controlled system coupled to a motorized therapeutic massage device being disposed within a mobile operations vehicle.

16. The device of claim 1, wherein the offset hub is directly coupled and rotationally coupled to the bearing assembly and thereby directly coupled and rotationally coupled to the contact surface arrangement.

17. A method of applying mechanical oscillating energy through human or animal muscle tissue, said method comprising:
contacting an area of skin covering human or animal muscle tissue, with an outer surface of a contact surface arrangement of a mechanical oscillation treatment device having an enclosure;
applying power to a motor having a motor drive shaft coupled to a transfer member having an offset hub that is directly coupled to and rotationally coupled to a bearing assembly and thereby rotationally coupled to the contact surface arrangement of said mechanical oscillation treatment device while said outer surface of the contact surface arrangement is in contact with the area of skin covering the human or animal muscle tissue, rotationally driving the contact surface arrangement to impart rotational motion including both random orbital oscillating motion and percussive motion to an outer surface of the contact surface arrangement;
with the rotationally moving outer surface of the contact surface arrangement of the device contacting with, while moving laterally relative to, a surface of a skin of a human or animal and being pressed into the skin and subcutaneous human or animal muscle tissue underlying the skin, imparting to the skin and subcutaneous muscle tissue random orbital oscillating mechanical shockwave energy by rotationally moving and oscillating, with the powered motor, the outer surface of the contact surface arrangement in at least one direction of approximately parallel to the surface of the area of skin, or
approximately perpendicular to the surface of the area of skin, or
having both parallel and perpendicular components to the surface of the area of skin,
in a random orbital mechanical motion having a variable orbit diameter to induce shearing and stretching forces in the muscle tissue;
detecting, with sensors and a solid state controller responsive to executing computer instructions in the mechanical oscillation treatment device, temperature of the contact surface arrangement;
generating, with the solid state controller, temperature data from the respective detected temperature of the contact surface arrangement;
storing, with the solid state controller, the temperature data;
communicating, with the solid state controller, the temperature data from the mechanical oscillation treatment device to a programmable computer that is external to the device; and
moving and directing air through the enclosure and thereby to and/or from the contact surface arrangement to cool the contact surface arrangement, wherein the moving and directing air is with a fan located in the enclosure.

18. The method of claim 17, wherein the communicating further comprising:
communicating the temperature data from the mechanical oscillation treatment device over a computer network to a remotely located programmable computer.

19. A motorized therapeutic massage device comprising:
an electrical motor having a motor drive shaft, disposed within an enclosure,
a contact surface arrangement coupled to said motor drive shaft, where the motor drive shaft is coupled to a transfer member having an offset hub that is directly coupled to and rotationally coupled to a bearing assembly and thereby rotationally coupled to the contact surface arrangement, a center axis of the motor drive shaft being offset from a center axis of the contact surface arrangement,
wherein the motor and driveshaft are coupled to the contact surface arrangement to rotationally drive the contact surface arrangement to impart rotational motion including random orbital oscillating motion and percussive motion to an outer surface of the contact surface arrangement,
wherein the contact surface arrangement is adapted to, in response to the motor and driveshaft rotational drive force rotationally driving the contact surface arrangement while contacting with, and moving laterally relative to, a surface of a skin of a human or animal and being pressed into the skin and subcutaneous human or animal muscle tissue underlying the skin, imparting to the skin and subcutaneous muscle tissue mechanical oscillating percussive shockwaves that penetrate the skin and subcutaneous muscle tissue to induce shearing and stretching forces in the muscle tissue,
an accessory mount, mechanically coupled to the enclosure, for attaching and removably mounting the motorized therapeutic massage device to at least one of: a massage chair, a wall mount, a robotically controlled system, or any combination thereof, and
wherein a first set of vent holes in at least one wall of the enclosure is arranged on one side of a cooling fan located within the enclosure and the contact surface arrangement is arranged on an opposite side of the cooling fan to move and direct air through the enclosure and thereby to and/or from the contact surface arrangement to cool the contact surface arrangement.

20. A motorized therapeutic massage device comprising:

an electrical motor having a motor drive shaft disposed within an enclosure;

a contact surface arrangement coupled to said motor drive shaft, where the motor drive shaft is coupled to a transfer member having an offset hub that is directly coupled to and rotationally coupled to a bearing assembly and thereby rotationally coupled to the contact surface arrangement, a center axis of the motor drive shaft being offset from a center axis of the contact surface arrangement;

wherein the electrical motor and driveshaft are coupled to the contact surface arrangement to rotationally drive the contact surface arrangement to impart rotational motion including both random orbital oscillating motion and percussive motion to an outer surface of the contact surface arrangement;

wherein the contact surface arrangement is adapted to, in response to the motor and driveshaft rotational drive force rotationally driving the contact surface arrangement, and while the rotationally moving outer surface of the contact surface arrangement is contacting with, while moving laterally relative to, a skin of a human or animal and being pressed into the skin and subcutaneous human or animal muscle tissue underlying the skin, imparting to the skin and subcutaneous muscle tissue mechanical oscillating percussive shockwaves for penetrating the skin and subcutaneous muscle tissue to induce shearing and stretching forces in the muscle tissue; and wherein a set of vent holes provided in the contact surface arrangement operate to have air pulled through the set of vent holes to cool the contact surface arrangement while the contact surface arrangement is rotationally moving.

21. The motorized therapeutic massage device of claim 20, wherein the contact surface arrangement includes, disposed adjacent to each other:

a massage pad mounting plate, a massage pad, and a massage pad cover that directly contacts the skin of a human or animal, and wherein the set of vent holes being arranged in the massage pad mounting plate and in the massage pad and operate to have air pulled through the set of vent holes to cool the massage pad and the massage pad cover while the contact surface arrangement is rotationally moving.

* * * * *